(12) United States Patent
Wiederanders et al.

(10) Patent No.: US 7,179,795 B2
(45) Date of Patent: Feb. 20, 2007

(54) NUCLEIC ACIDS ENCODING CHIMERIC PROTEINS COMPRISING BMP-2 AND A PROTEINASE INHIBITOR

(75) Inventors: Bernd Wiederanders, Jena-Cospeda (DE); Gunter Maubach, Jena (DE)

(73) Assignee: Depuy Biotech Jena GmbH, Jena (DE)

( * ) Notice: Subject to any disclaimer, the term of this patent is extended or adjusted under 35 U.S.C. 154(b) by 0 days.

(21) Appl. No.: 10/257,384

(22) PCT Filed: Apr. 18, 2001

(86) PCT No.: PCT/DE01/01510

§ 371 (c)(1), (2), (4) Date: Feb. 3, 2003

(87) PCT Pub. No.: WO01/78756

PCT Pub. Date: Oct. 25, 2001

(65) Prior Publication Data

US 2004/0087524 A1 May 6, 2004

(30) Foreign Application Priority Data

Apr. 18, 2000 (DE) .............................. 100 20 125

(51) Int. Cl.
| | |
|---|---|
| A01N 43/00 | (2006.01) |
| A61K 31/70 | (2006.01) |
| C07K 1/00 | (2006.01) |
| C07K 14/00 | (2006.01) |
| C07K 17/00 | (2006.01) |
| C07H 21/04 | (2006.01) |
| C07H 21/02 | (2006.01) |
| A01N 63/00 | (2006.01) |
| A01N 65/00 | (2006.01) |

(52) U.S. Cl. ...................... 514/44; 424/93.1; 536/23.1; 530/350

(58) Field of Classification Search .................. 514/44; 424/93.1; 800/8; 536/23.1, 23.4, 24.2
See application file for complete search history.

(56) References Cited

U.S. PATENT DOCUMENTS 5,935,935 A * 8/1999 Connelly et al. ............. 514/44
5,942,496 A 8/1999 Bonadio et al. ............... 514/44
5,962,427 A 10/1999 Goldstein et al. ............. 514/44

FOREIGN PATENT DOCUMENTS

| EP | 0 504 938 A2 | 9/1992 |
| EP | 0 704 532 A2 | 4/1996 |
| WO | WO 91/19510 | 12/1991 |
| WO | WO 98/51788 | 11/1998 |
| WO | WO 98/55137 | 12/1998 |
| WO | WO 01/078756 A3 | 10/2001 |

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Neaud, et al. (2000) J. Biol. Chem., 275(45): 35565-69.*
Zhang, et al. (2003) Oncogene, 22: 974-82.*
Gafni, et al. (2004) Molecular Therapy, 9(4): 587-95.*
Hughes (2004) J. Surg. Oncol., 85: 28-35.*
Taguchi S et al: Microbial secretion of biologically active human transforming growth factor alpha fused to the Streptomyces protease inhibitor; vol. 159, No. 2, (Jul. 4, 1995), pp. 239-243. XP002173729 figure 2C.
Kolkhorst V et al: Inhibition of tumour cell invasion by protease inhibitors: correlation with the protease profile; J Cancer Res Clin Oncol., vol. 124, No. 11, 1998, pp. 598-606, XP002179730.

* cited by examiner

*Primary Examiner*—Joseph Woitach
*Assistant Examiner*—Robert M. Kelly
(74) *Attorney, Agent, or Firm*—Joyce Von Natzmer; Hall, Vande Sande & Pequignot LLP

(57) ABSTRACT

This invention relates to an agent for producing a pharmaceutical drug for postoperative use after removal of bone tumors produced from a nucleic acid by linking a known sequence for promoting bone growth and a known proteinase inhibitor by a variable spacer molecule. This linkage results in a novel bifunctional active ingredient combining both properties in a biological molecule. This invention is used in the medical field, in particular in the specialty field of orthopedics.

18 Claims, 3 Drawing Sheets

Figures 1, 2:
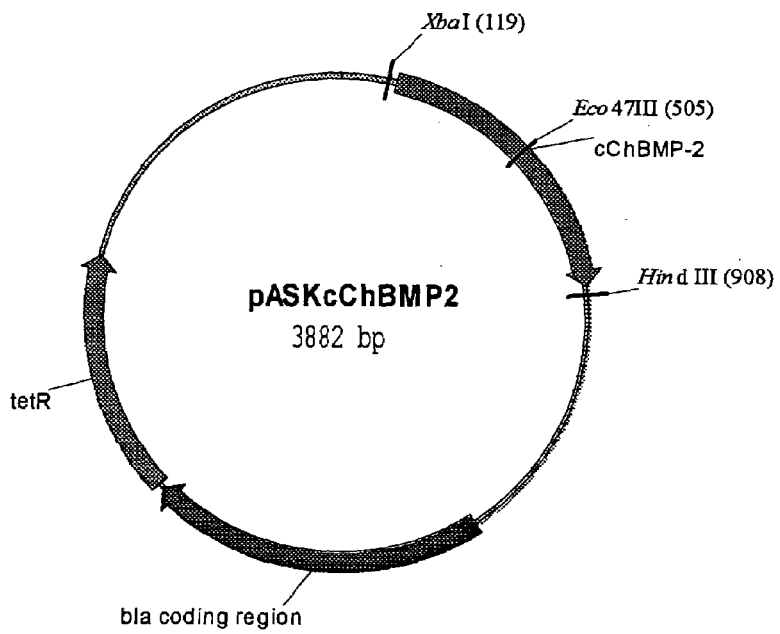

Primer for polymerase chain reaction (PCR):

A: 5' GAC GAT CTA GAT AAC GAG GGC AAA AAA TGT CCA GTC CCG GCA AGC CGC C 3'

B: 5' CAG GTC AAG CTT CTA GCG ACA CCC ACA ACC C 3'

C: 5' ACC ACG GAT CCT CCA GTC CCG GCA AGC C 3'

D: 5' CCG CCA AGC TTC TAG CGA CAC CCA CAA CCC 3'

D': 5' CCT CCA AGC TTC TAA TGA TGG TGA TGG TGA TGG CGA CAC CCA CAA CCC 3'

SEQ ID NO: 1

AGC GCT AGC CAT CAC CAT CAC CAT CAT GGC GCC GAG ACC GCA
Ser Ala Ser His His His His His His Gly Ala Glu Thr Ala

SEQ ID NO: 2

AGC GGT GGC GGT GGC GGT
Ser Gly Gly Gly Gly Gly

SEQ ID NO: 3

AGC GGT GTT GGT TCT GGT CCG GGT
Ser Gly Val Gly Ser Gly Pro Gly

SEQ ID NO: 4

AGC GAA CAA AAA CTC ATC TCA GAA GAG GAT CTG
Ser Glu Gln Lys Leu Ile Ser Glu Glu Asp Leu

SEQ ID NO: 5

AGC AAC GTT GGT TCT GGT CCG GGT
Ser Asn Val Gly Ser Gly Pro Gly

Fig. 3

SEQUENCE LISTING

<160> NUMBER OF SEQ ID NOS: 19

<210> SEQ ID NO 1
<211> LENGTH: 7373
<212> TYPE: DNA
<213> ORGANISM: Artificial Sequence
<220> FEATURE:
<223> OTHER INFORMATION: Expression vector pMalc2cchbmp2
<220> FEATURE:
<221> NAME/KEY: CDS
<222> LOCATION: (1528)..(3453)
<223> OTHER INFORMATION: /product = fusion protein MBP Cystatin C BMP-2
<220> FEATURE:
<221> NAME/KEY: misc_feature
<222> LOCATION: (2689)

```
<223> OTHER INFORMATION: Faktor Xa Protease /position=388
      (Amino acid sequence)
<220> FEATURE:
<221> NAME/KEY: misc_feature
<222> LOCATION: (3067)..(3108)
<223> OTHER INFORMATION: /spacer between Cystatin C andBMP-2
<300> PUBLICATION INFORMATION:
<301> AUTHORS: Zwick, M B.
<302> TITLE: Expression vector pMal-X, complete sequence
<303> JOURNAL: Anal. Biochem.
<304> VOLUME: 264
<305> ISSUE: 1
<306> PAGES: 87-97
<307> DATE: 1998-11-01
<308> DATABASE ACCESSION NUMBER: Entrez Nucleotide database/AF031813
<309> DATABASE ENTRY DATE: 2001-05-07
<313> RELEVANT RESIDUES: 1528 - 3453

<400> SEQUENCE: 1
```

| | | |
|---|---|---|
| ccgacaccat cgaatggtgc aaaacctttc gcggtatggc atgatagcgc ccggaagaga | 60 |
| gtcaattcag gtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |
| atgagggcat cgttcccact gcgatgctgg ttgccaacga tcagatggcg ctgggcgcaa | 840 |
| tgcgcgccat taccgagtcc gggctgcgcg ttggtgcgga tatctcggta gtgggatacg | 900 |
| acgataccga agacagctca tgttatatcc cgccgttaac caccatcaaa caggattttc | 960 |
| gcctgctggg gcaaaccagc gtggaccgct tgctgcaact ctctcagggc caggcggtga | 1020 |
| agggcaatca gctgttgccc gtctcactgg tgaaaagaaa aaccaccctg gcgcccaata | 1080 |
| cgcaaaccgc ctctccccgc gcgttggccg attcattaat gcagctggca cgacaggttt | 1140 |
| cccgactgga aagcgggcag tgagcgcaac gcaattaatg tgagttagct cactcattag | 1200 |
| gcacaattct catgtttgac agcttatcat cgactgcacg gtgcaccaat gcttctggcg | 1260 |
| tcaggcagcc atcggaagct gtggtatggc tgtgcaggtc gtaaatcact gcataattcg | 1320 |
| tgtcgctcaa ggcgcactcc cgttctggat aatgttttt cgccgacat cataacggtt | 1380 |
| ctggcaaata ttctgaaatg agctgttgac aattaatcat cggctcgtat aatgtgtgga | 1440 |
| attgtgagcg gataacaatt tcacacagga acagccagt ccgtttaggt gttttcacga | 1500 |
| gcacttcacc aacaaggacc atagatt atg aaa atc gaa gaa ggt aaa ctg gta | 1554 |
|                              Met Lys Ile Glu Glu Gly Lys Leu Val | |
|                               1               5                   | |
| atc tgg att aac ggc gat aaa ggc tat aac ggt ctc gct gaa gtc ggt | 1602 |
| Ile Trp Ile Asn Gly Asp Lys Gly Tyr Asn Gly Leu Ala Glu Val Gly | |
|  10              15              20              25              | |
| aag aaa ttc gag aaa gat acc gga att aaa gtc acc gtt gag cat ccg | 1650 |

-continued

```
                Lys Lys Phe Glu Lys Asp Thr Gly Ile Lys Val Thr Val Glu His Pro
                            30                  35                  40 gat aaa ctg gaa gag aaa ttc cca cag gtt gcg gca act ggc gat ggc        1698
Asp Lys Leu Glu Glu Lys Phe Pro Gln Val Ala Ala Thr Gly Asp Gly
            45                  50                  55 cct gac att atc ttc tgg gca cac gac cgc ttt ggt ggc tac gct caa        1746
Pro Asp Ile Ile Phe Trp Ala His Asp Arg Phe Gly Gly Tyr Ala Gln
60                  65                  70 tct ggc ctg ttg gct gaa atc acc ccg gac aaa gcg ttc cag gac aag        1794
Ser Gly Leu Leu Ala Glu Ile Thr Pro Asp Lys Ala Phe Gln Asp Lys
    75                  80                  85 ctg tat ccg ttt acc tgg gat gcc gta cgt tac aac ggc aag ctg att        1842
Leu Tyr Pro Phe Thr Trp Asp Ala Val Arg Tyr Asn Gly Lys Leu Ile
90                  95                  100                 105 gct tac ccg atc gct gtt gaa gcg tta tcg ctg att tat aac aaa gat        1890
Ala Tyr Pro Ile Ala Val Glu Ala Leu Ser Leu Ile Tyr Asn Lys Asp
            110                 115                 120 ctg ctg ccg aac ccg cca aaa acc tgg gaa gag atc ccg gcg ctg gat        1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa        1986
Lys Glu Leu Lys Ala Lys Gly Lys Ser Ala Leu Met Phe Asn Leu Gln
            140                 145                 150 gaa ccg tac ttc acc tgg ccg ctg att gct gct gac ggg ggt tat gcg        2034
Glu Pro Tyr Phe Thr Trp Pro Leu Ile Ala Ala Asp Gly Gly Tyr Ala
        155                 160                 165 ttc aag tat gaa aac ggc aag tac gac att aaa gac gtg ggc gtg gat        2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa        2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc        2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg        2226
Phe Asn Lys Gly Glu Thr Ala Met Thr Ile Asn Gly Pro Trp Ala Trp
            220                 225                 230 tcc aac atc gac acc agc aaa gtg aat tat ggt gta acg gta ctg ccg        2274
Ser Asn Ile Asp Thr Ser Lys Val Asn Tyr Gly Val Thr Val Leu Pro
        235                 240                 245 acc ttc aag ggt caa cca tcc aaa ccg ttc gtt ggc gtg ctg agc gca        2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc        2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac        2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg        2466
Lys Pro Leu Gly Ala Val Ala Leu Lys Ser Tyr Glu Glu Glu Leu Ala
            300                 305                 310 aaa gat cca cgt att gcc gcc acc atg gaa aac gcc cag aaa ggt gaa        2514
Lys Asp Pro Arg Ile Ala Ala Thr Met Glu Asn Ala Gln Lys Gly Glu
            315                 320                 325 atc atg ccg aac atc ccg cag atg tcc gct ttc tgg tat gcc gtg cgt        2562
Ile Met Pro Asn Ile Pro Gln Met Ser Ala Phe Trp Tyr Ala Val Arg
330                 335                 340                 345
```

```
act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
            350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc gga tcc    2706
Asn Asn Asn Asn Leu Gly Ile Glu Gly Arg Ile Ser Glu Phe Gly Ser
            380                 385                 390 tcc agt ccc ggc aag ccg ccg cgc ctg gtg gga ggc ccc atg gac gcc    2754
Ser Ser Pro Gly Lys Pro Pro Arg Leu Val Gly Gly Pro Met Asp Ala
            395                 400                 405 agc gtg gag gag gag ggt gtg cgg cgt gca ctg gac ttt gcc gtc ggc    2802
Ser Val Glu Glu Glu Gly Val Arg Arg Ala Leu Asp Phe Ala Val Gly
410                 415                 420                 425 gag tac aac aaa gcc agc aac gac atg tac cac agc cgc gcg ctg cag    2850
Glu Tyr Asn Lys Ala Ser Asn Asp Met Tyr His Ser Arg Ala Leu Gln
                430                 435                 440 gtg gtg cgc gcc cgc aag cag atc gta gct ggg gtg aac tac ttc ttg    2898
Val Val Arg Ala Arg Lys Gln Ile Val Ala Gly Val Asn Tyr Phe Leu
            445                 450                 455 gac gtg gag ctg ggc cga acc acg tgt acc aag acc cag ccc aac ttg    2946
Asp Val Glu Leu Gly Arg Thr Thr Cys Thr Lys Thr Gln Pro Asn Leu
            460                 465                 470 gac aac tgc ccc ttc cat gac cag cca cat ctg aaa agg aaa gca ttc    2994
Asp Asn Cys Pro Phe His Asp Gln Pro His Leu Lys Arg Lys Ala Phe
            475                 480                 485 tgc tct ttc cag atc tac gct gtg cct tgg cag ggc aca atg acc ttg    3042
Cys Ser Phe Gln Ile Tyr Ala Val Pro Trp Gln Gly Thr Met Thr Leu
490                 495                 500                 505 tcg aaa tcc acc tgt cag gac gcc agc gct agc cat cac cat cac cat    3090
Ser Lys Ser Thr Cys Gln Asp Ala Ser Ala Ser His His His His His
                510                 515                 520 cat ggc gcc gag acc gca caa gcc aaa cac aaa cag cgg aaa cgc ctt    3138
His Gly Ala Glu Thr Ala Gln Ala Lys His Lys Gln Arg Lys Arg Leu
            525                 530                 535 aag tcc agc tgt aag aga cac cct ttg tac gtg gac ttc agt gac gtg    3186
Lys Ser Ser Cys Lys Arg His Pro Leu Tyr Val Asp Phe Ser Asp Val
            540                 545                 550 ggg tgg aat gac tgg att gtg gct ccc ccg ggg tat cac gcc ttt tac    3234
Gly Trp Asn Asp Trp Ile Val Ala Pro Pro Gly Tyr His Ala Phe Tyr
            555                 560                 565 tgc cac gga gaa tgc cct ttt cct ctg gct gat cat ctg aac tcc act    3282
Cys His Gly Glu Cys Pro Phe Pro Leu Ala Asp His Leu Asn Ser Thr
570                 575                 580                 585 aat cat gcc att gtt cag acg ttg gtc aac tct gtt aac tct aag att    3330
Asn His Ala Ile Val Gln Thr Leu Val Asn Ser Val Asn Ser Lys Ile
                590                 595                 600 cct aag gca tgc tgt gtc ccg aca gaa ctc agt gct atc tcg atg ctg    3378
Pro Lys Ala Cys Cys Val Pro Thr Glu Leu Ser Ala Ile Ser Met Leu
            605                 610                 615 tac ctt gac gag aat gaa aag gtt gta tta aag aac tat cag gac atg    3426
Tyr Leu Asp Glu Asn Glu Lys Val Val Leu Lys Asn Tyr Gln Asp Met
            620                 625                 630 gtt gtg gag ggt tgt ggg tgt cgc tag aagcttggca ctggccgtcg          3473
Val Val Glu Gly Cys Gly Cys Arg
            635                 640 ttttacaacg tcgtgactgg gaaaccctg gcgttaccca acttaatcgc cttgcagcac    3533 atccccttt cgccagctgg cgtaatagcg aagaggcccg caccgatcgc ccttcccaac    3593
```

```
agttgcgcag cctgaatggc gaatggcagc ttggctgttt tggcggatga gataagattt    3653
tcagcctgat acagattaaa tcagaacgca gaagcggtct gataaaacag aatttgcctg    3713
gcggcagtag cgcggtggtc ccacctgacc ccatgccgaa ctcagaagtg aaacgccgta    3773
gcgccgatgg tagtgtgggg tctccccatg cgagagtagg gaactgccag gcatcaaata    3833
aaacgaaagg ctcagtcgaa agactgggcc tttcgtttta tctgttgttt gtcggtgaac    3893
gctctcctga gtaggacaaa tccgccggga gcggatttga acgttgcgaa gcaacggccc    3953
ggagggtggc gggcaggacg cccgccataa actgccaggc atcaaattaa gcagaaggcc    4013
atcctgacgg atggcctttt tgcgttctta caaactcttt ttgtttattt ttctaaatac    4073
attcaaatat gtatccgctc atgagacaat aaccctgata aatgcttcaa taatattgaa    4133
aaaggaagag tatgagtatt caacatttcc gtgtcgccct tattccctt tttgcggcat     4193
tttgccttcc tgttttttgct cacccagaaa cgctggtgaa agtaaaagat gctgaagatc    4253
agttgggtgc acgagtgggt tacatcgaac tggatctcaa cagcggtaag atccttgaga    4313
gttttcgccc cgaagaacgt tctccaatga tgagcacttt taaagttctg ctatgtggcg    4373
cggtattatc ccgtgttgac gccgggcaag agcaactcgg tcgccgcata cactattctc    4433
agaatgactt ggttgagtac tcaccagtca cagaaaagca tcttacggat ggcatgacag    4493
taagagaatt atgcagtgct gccataacca tgagtgataa cactgcggcc aacttacttc    4553
tgacaacgat cggaggaccg aaggagctaa ccgcttttt tgcacaacatg ggggatcatg     4613
taactcgcct tgatcgttgg gaaccggagc tgaatgaagc cataccaaac gacgagcgtg    4673
acaccacgat gcctgtagca atggcaacaa cgttgcgcaa actattaact ggcgaactac    4733
ttactctagc ttcccggcaa caattaatag actggatgga ggcggataaa gttgcaggac    4793
cacttctgcg ctcggccctt ccggctggct ggtttattgc tgataaatct ggagccggtg    4853
agcgtgggtc tcgcggtatc attgcagcac tggggccaga tggtaagccc tcccgtatcg    4913
tagttatcta cacgacgggg agtcaggcaa ctatggatga acgaaataga cagatcgctg    4973
agataggtgc ctcactgatt aagcattggt aactgtcaga ccaagtttac tcatatatac    5033
tttagattga tttaccccgg ttgataatca gaaaagcccc aaaaacagga agattgtata    5093
agcaaatatt taaattgtaa acgttaatat tttgttaaaa ttcgcgttaa attttttgtta    5153
aatcagctca tttttaacc aataggccga atcggcaaa atcccttata aatcaaaaga      5213
atagcccgag atagggttga gtgttgttcc agtttggaac aagagtccac tattaaagaa    5273
cgtggactcc aacgtcaaag ggcgaaaaac cgtctatcag ggcgatggcc cactacgtga    5333
accatcaccc aaatcaagtt ttttggggtc gaggtgccgt aaagcactaa atcggaaccc    5393
taaagggagc ccccgattta gagcttgacg gggaaagccg gcgaacgtgg cgagaaagga    5453
agggaagaaa gcgaaaggag cgggcgctag ggcgctggca agtgtagcgg tcacgctgcg    5513
cgtaaccacc acacccgccg cgcttaatgc gccgctacag ggcgcgtaaa aggatctagg    5573
tgaagatcct tttgataat ctcatgacca aaatcccta acgtgagttt tcgttccact       5633
gagcgtcaga ccccgtagaa aagatcaaag gatcttcttg agatcctttt tttctgcgcg    5693
taatctgctg cttgcaaaca aaaaaaccac cgctaccagc ggtggtttgt ttgccggatc    5753
aagagctacc aactctttt ccgaaggtaa ctggcttcag cagagcgcag ataccaaata     5813
ctgtccttct agtgtagccg tagttaggcc accacttcaa gaactctgta gcaccgccta    5873
catacctcgc tctgctaatc ctgttaccag tggctgctgc cagtggcgat aagtcgtgtc    5933
```

```
ttaccgggtt ggactcaaga cgatagttac cggataaggc gcagcggtcg ggctgaacgg    5993
ggggttcgtg cacacagccc agcttggagc gaacgaccta caccgaactg agatacctac    6053
agcgtgagct atgagaaagc gccacgcttc ccgaagggag aaaggcggac aggtatccgg    6113
taagcggcag ggtcggaaca ggagagcgca cgagggagct tccaggggga aacgcctggt    6173
atctttatag tcctgtcggg tttcgccacc tctgacttga gcgtcgattt ttgtgatgct    6233
cgtcagggg gcggagccta tggaaaaacg ccagcaacgc ggccttttta cggttcctgg    6293
cctttttgctg gccttttgct cacatgttct ttcctgcgtt atcccctgat tctgtggata    6353
accgtattac cgcctttgag tgagctgata ccgctcgccg cagccgaacg accgagcgca    6413
gcgagtcagt gagcgaggaa gcggaagagc gcctgatgcg gtattttctc cttacgcatc    6473
tgtgcggtat ttcacaccgc atatggtgca ctctcagtac aatctgctct gatgccgcat    6533
agttaagcca gtatacactc cgctatcgct acgtgactgg gtcatggctg cgccccgaca    6593
cccgccaaca cccgctgacg cgccctgacg ggcttgtctg ctcccggcat ccgcttacag    6653
acaagctgtg accgtctccg ggagctgcat gtgtcagagg ttttcaccgt catcaccgaa    6713
acgcgcgagg cagctgcggt aaagctcatc agcgtggtcg tgcagcgatt cacagatgtc    6773
tgcctgttca tccgcgtcca gctcgttgag tttctccaga agcgttaatg tctggcttct    6833
gataaagcgg gccatgttaa gggcggtttt tccctgtttg gtcacttgat gcctccgtgt    6893
aaggggggaat ttctgttcat ggggggtaatg ataccgatga acgagagag gatgctcacg    6953
atacgggtta ctgatgatga acatgcccgg ttactggaac gttgtgaggg taaacaactg    7013
gcggtatgga tgcggcggga ccagagaaaa atcactcagg gtcaatgcca gcgcttcgtt    7073
aatacagatg taggtgttcc acagggtagc cagcagcatc ctgcgatgca gatccggaac    7133
ataatggtgc agggcgctga cttccgcgtt tccagacttt acgaaacacg gaaaccgaag    7193
accattcatg ttgttgctca ggtcgcagac gttttgcagc agcagtcgct tcacgttcgc    7253
tcgcgtatcg gtgattcatt ctgctaacca gtaaggcaac cccgccagcc tagccgggtc    7313
ctcaacgaca ggagcacgat catgcgcacc cgtggccagg acccaacgct gcccgaaatt    7373
```

<210> SEQ ID NO 2
<211> LENGTH: 641
<212> TYPE: PRT
<213> ORGANISM: Artificial Sequence
<220> FEATURE:
<223> OTHER INFORMATION: Expression vector pMalc2cchbmp2

<400> SEQUENCE: 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110
```

```
Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg Ile Ser Glu Phe Gly Ser Ser Pro Gly Lys Pro Pro
385                 390                 395                 400

Arg Leu Val Gly Gly Pro Met Asp Ala Ser Val Glu Glu Gly Val
                405                 410                 415

Arg Arg Ala Leu Asp Phe Ala Val Gly Glu Tyr Asn Lys Ala Ser Asn
                420                 425                 430

Asp Met Tyr His Ser Arg Ala Leu Gln Val Val Arg Ala Arg Lys Gln
        435                 440                 445

Ile Val Ala Gly Val Asn Tyr Phe Leu Asp Val Glu Leu Gly Arg Thr
        450                 455                 460

Thr Cys Thr Lys Thr Gln Pro Asn Leu Asp Asn Cys Pro Phe His Asp
465                 470                 475                 480

Gln Pro His Leu Lys Arg Lys Ala Phe Cys Ser Phe Gln Ile Tyr Ala
                485                 490                 495

Val Pro Trp Gln Gly Thr Met Thr Leu Ser Lys Ser Thr Cys Gln Asp
                500                 505                 510

Ala Ser Ala Ser His His His His His Gly Ala Glu Thr Ala Gln
        515                 520                 525

Ala Lys His Lys Gln Arg Lys Arg Leu Lys Ser Ser Cys Lys Arg His
```

```
                530              535             540
Pro Leu Tyr Val Asp Phe Ser Asp Val Gly Trp Asn Asp Trp Ile Val
545                 550                 555                 560

Ala Pro Pro Gly Tyr His Ala Phe Tyr Cys His Gly Glu Cys Pro Phe
                565                 570                 575

Pro Leu Ala Asp His Leu Asn Ser Thr Asn His Ala Ile Val Gln Thr
            580                 585                 590

Leu Val Asn Ser Val Asn Ser Lys Ile Pro Lys Ala Cys Cys Val Pro
        595                 600                 605

Thr Glu Leu Ser Ala Ile Ser Met Leu Tyr Leu Asp Glu Asn Glu Lys
    610                 615                 620

Val Val Leu Lys Asn Tyr Gln Asp Met Val Val Glu Gly Cys Gly Cys
625                 630                 635                 640

Arg

<210> SEQ ID NO 3
<211> LENGTH: 3882
<212> TYPE: DNA
<213> ORGANISM: Artificial Sequence
<220> FEATURE:
<223> OTHER INFORMATION: Description of artificial sequence:
      Expression vector pASKcChBMP2
<220> FEATURE:
<221> NAME/KEY: CDS
<222> LOCATION: (139)..(885)
<223> OTHER INFORMATION: /product = fusion protein Cystatin C BMP-2
<220> FEATURE:
<221> NAME/KEY: misc_feature
<222> LOCATION: (502)..(543)
<223> OTHER INFORMATION: /spacer between Cystatin C and BMP-2

<400> SEQUENCE: 3
ccatcgaatg gccagatgat taattcctaa ttttgttga cactctatca ttgatagagt      60
tattttacca ctccctatca gtgatagaga aagtgaaat gaatagttcg acaaaaatct    120
agataacgag ggcaaaaa atg tcc agt ccc ggc aag ccg ccg cgc ctg gtg    171
                    Met Ser Ser Pro Gly Lys Pro Pro Arg Leu Val
                     1               5                      10 gga ggc ccc atg gac gcc agc gtg gag gag gag ggt gtg cgg cgt gca    219
Gly Gly Pro Met Asp Ala Ser Val Glu Glu Glu Gly Val Arg Arg Ala
            15                  20                  25 ctg gac ttt gcc gtc ggc gag tac aac aaa gcc agc aac gac atg tac    267
Leu Asp Phe Ala Val Gly Glu Tyr Asn Lys Ala Ser Asn Asp Met Tyr
        30                  35                  40 cac agc cgc gcg ctg cag gtg gtg cgc gcc cgc aag cag atc gta gct    315
His Ser Arg Ala Leu Gln Val Val Arg Ala Arg Lys Gln Ile Val Ala
    45                  50                  55 ggg gtg aac tac ttc ttg gac gtg gag ctg ggc cga acc acg tgt acc    363
Gly Val Asn Tyr Phe Leu Asp Val Glu Leu Gly Arg Thr Thr Cys Thr
60                  65                  70                  75 aag acc cag ccc aac ttg gac aac tgc ccc ttc cat gac cag cca cat    411
Lys Thr Gln Pro Asn Leu Asp Asn Cys Pro Phe His Asp Gln Pro His
                80                  85                  90 ctg aaa agg aaa gca ttc tgc tct ttc cag atc tac gct gtg cct tgg    459
Leu Lys Arg Lys Ala Phe Cys Ser Phe Gln Ile Tyr Ala Val Pro Trp
            95                  100                 105 cag ggc aca atg acc ttg tcg aaa tcc acc tgt cag gac gcc agc gct    507
Gln Gly Thr Met Thr Leu Ser Lys Ser Thr Cys Gln Asp Ala Ser Ala
        110                 115                 120 agc cat cac cat cac cat cat ggc gcc gag acc gca caa gcc aaa cac    555
Ser His His His His His His Gly Ala Glu Thr Ala Gln Ala Lys His
```

-continued

| | | | | | 125 | | | | | 130 | | | | | 135 | | |
|---|---|---|---|---|---|---|---|---|---|---|---|---|---|---|---|---|---|
| aaa | cag | cgg | aaa | cgc | ctt | aag | tcc | agc | tgt | aag | aga | cac | cct | ttg | tac | | 603 |
| Lys | Gln | Arg | Lys | Arg | Leu | Lys | Ser | Ser | Cys | Lys | Arg | His | Pro | Leu | Tyr | | |
| 140 | | | | | 145 | | | | | 150 | | | | | 155 | | |
| gtg | gac | ttc | agt | gac | gtg | ggg | tgg | aat | gac | tgg | att | gtg | gct | ccc | ccg | | 651 |
| Val | Asp | Phe | Ser | Asp | Val | Gly | Trp | Asn | Asp | Trp | Ile | Val | Ala | Pro | Pro | | |
| | | | | 160 | | | | | 165 | | | | | 170 | | | |
| ggg | tat | cac | gcc | ttt | tac | tgc | cac | gga | gaa | tgc | cct | ttt | cct | ctg | gct | | 699 |
| Gly | Tyr | His | Ala | Phe | Tyr | Cys | His | Gly | Glu | Cys | Pro | Phe | Pro | Leu | Ala | | |
| | | | 175 | | | | | 180 | | | | | 185 | | | | |
| gat | cat | ctg | aac | tcc | act | aat | cat | gcc | att | gtt | cag | acg | ttg | gtc | aac | | 747 |
| Asp | His | Leu | Asn | Ser | Thr | Asn | His | Ala | Ile | Val | Gln | Thr | Leu | Val | Asn | | |
| | | 190 | | | | | 195 | | | | | 200 | | | | | |
| tct | gtt | aac | tct | aag | att | cct | aag | gca | tgc | tgt | gtc | ccg | aca | gaa | ctc | | 795 |
| Ser | Val | Asn | Ser | Lys | Ile | Pro | Lys | Ala | Cys | Cys | Val | Pro | Thr | Glu | Leu | | |
| | 205 | | | | | 210 | | | | | 215 | | | | | | |
| agt | gct | atc | tcg | atg | ctg | tac | ctt | gac | gag | aat | gaa | aag | gtt | gta | tta | | 843 |
| Ser | Ala | Ile | Ser | Met | Leu | Tyr | Leu | Asp | Glu | Asn | Glu | Lys | Val | Val | Leu | | |
| 220 | | | | | 225 | | | | | 230 | | | | | 235 | | |
| aag | aac | tat | cag | gac | atg | gtt | gtg | gag | ggt | tgt | ggg | tgt | cgc | | | | 885 |
| Lys | Asn | Tyr | Gln | Asp | Met | Val | Val | Glu | Gly | Cys | Gly | Cys | Arg | | | | |
| | | | | 240 | | | | | 245 | | | | | | | | |

```
tagggtctct gatatctaac taagcttgac ctgtgaagtg aaaaatggcg cacattgtgc    945
gacatttttt ttgtctgccg tttaccgcta ctgcgtcacg gatctccacg cgccctgtag   1005
cggcgcatta agcgcggcgg gtgtggtggt tacgcgcagc gtgaccgcta cacttgccag   1065
cgccctagcg cccgctcctt tcgctttctt cccttccttt ctcgccacgt tcgccggctt   1125
tccccgtcaa gctctaaatc gggggctccc tttagggttc cgatttagtg ctttacggca   1185
cctcgacccc aaaaaacttg attagggtga tggttcacgt agtgggccat cgccctgata   1245
gacggttttt cgcccttga cgttggagtc cacgttcttt aatagtggac tcttgttcca   1305
aactggaaca acactcaacc ctatctcggt ctattctttt gatttataag ggattttgcc   1365
gatttcggcc tattggttaa aaaatgagct gatttaacaa aaatttaacg cgaattttaa   1425
caaaatatta acgcttacaa tttcaggtgg cacttttcgg ggaaatgtgc gcggaacccc   1485
tatttgttta ttttttctaaa tacattcaaa tatgtatccg ctcatgagac aataaccctg   1545
ataaatgctt caataatatt gaaaaaggaa gagtatgagt attcaacatt tccgtgtcgc   1605
ccttattccc ttttttgcgg catttttgcct tcctgttttt gctcacccag aaacgctggt   1665
gaaagtaaaa gatgctgaag atcagttggg tgcacgagtg gttacatcg aactggatct   1725
caacagcgt aagatccttg agagttttcg ccccgaagaa cgttttccaa tgatgagcac   1785
ttttaaagtt ctgctatgtg cgcggtatt atcccgtatt gacgccgggc aagagcaact   1845
cggtcgccgc atacactatt ctcagaatga cttggttgag tactcaccag tcacagaaaa   1905
gcatcttacg gatggcatga cagtaagaga attatgcagt gctgccataa ccatgagtga   1965
taacactgcg gccaacttac ttctgacaac gatcggagga ccgaaggagc taaccgcttt   2025
tttgcacaac atgggggatc atgtaactcg ccttgatcgt tgggaaccgg agctgaatga   2085
agccatacca aacgacgagc gtgacaccac gatgcctgta gcaatggcaa caacgttgcg   2145
caaactatta actggcgaac tacttactct agcttcccgg caacaattga tagactggat   2205
ggaggcggat aaagttgcag gaccacttct gcgctcggcc cttccggctg gctggtttat   2265
tgctgataaa tctggagccg gtgagcgtgg gctctcgcgt atcattgcag cactggggcc   2325
agatggtaag ccctcccgta tcgtagttat ctacacgacg gggagtcagg caactatgga   2385
```

-continued

```
tgaacgaaat agacagatcg ctgagatagg tgcctcactg attaagcatt ggtaggaatt    2445
aatgatgtct cgtttagata aaagtaaagt gattaacagc gcattagagc tgcttaatga    2505
ggtcggaatc gaaggtttaa caacccgtaa actcgcccag aagctaggtg tagagcagcc    2565
tacattgtat tggcatgtaa aaaataagcg ggctttgctc gacgccttag ccattgagat    2625
gttagatagg caccatactc acttttgccc tttagaaggg gaaagctggc aagattttt    2685 acgtaataac gctaaaagtt ttagatgtgc tttactaagt catcgcgatg gagcaaaagt    2745
acatttaggt acacggccta cagaaaaaca gtatgaaact ctcgaaaatc aattagcctt    2805
tttatgccaa caaggttttt cactagagaa tgcattatat gcactcagcg cagtggggca    2865
ttttacttta ggttgcgtat tggaagatca agagcatcaa gtcgctaaag aagaaaggga    2925
aacacctact actgatagta tgccgccatt attacgacaa gctatcgaat tatttgatca    2985
ccaaggtgca gagccagcct tcttattcgg ccttgaattg atcatatgcg gattagaaaa    3045
acaacttaaa tgtgaaagtg ggtcttaaaa gcagcataac cttttccgt gatggtaact    3105 tcactagttt aaaaggatct aggtgaagat ccttttttgat aatctcatga ccaaaatccc    3165
ttaacgtgag ttttcgttcc actgagcgtc agacccccgta gaaaagatca aggatcttc    3225 ttgagatcct ttttttctgc gcgtaatctg ctgcttgcaa acaaaaaaac caccgctacc    3285
agcggtggtt tgtttgccgg atcaagagct accaactctt tttccgaagg taactggctt    3345
cagcagagcg cagataccaa atactgtcct tctagtgtag ccgtagttag gccaccactt    3405
caagaactct gtagcaccgc ctacatacct cgctctgcta atcctgttac cagtggctgc    3465
tgccagtggc gataagtcgt gtcttaccgg gttggactca agacgatagt taccggataa    3525
ggcgcagcgg tcgggctgaa cggggggttc gtgcacacag cccagcttgg agcgaacgac    3585
ctacaccgaa ctgagatacc tacagcgtga gctatgagaa agcgccacgc ttcccgaagg    3645
gagaaaggcg gacaggtatc cggtaagcgg cagggtcgga acaggagagc gcacgaggga    3705
gcttccaggg ggaaacgcct ggtatcttta tagtcctgtc gggtttcgcc acctctgact    3765
tgagcgtcga ttttgtgat gctcgtcagg ggggcggagc ctatgaaaaa acgccagcaa    3825
cgcggccttt ttacggttcc tggccttttg ctggcctttt gctcacatga cccgaca       3882
```

<210> SEQ ID NO 4
<211> LENGTH: 249
<212> TYPE: PRT
<213> ORGANISM: Artificial Sequence
<220> FEATURE:
<223> OTHER INFORMATION: Description of artificial sequence:
      Expression vector pASKcChBMP2

<400> SEQUENCE: 4

```
Met Ser Ser Pro Gly Lys Pro Pro Arg Leu Val Gly Pro Met Asp
1               5                   10                  15

Ala Ser Val Glu Glu Gly Val Arg Arg Ala Leu Asp Phe Ala Val
                20                  25                  30

Gly Glu Tyr Asn Lys Ala Ser Asn Asp Met Tyr His Ser Arg Ala Leu
            35                  40                  45

Gln Val Val Arg Ala Arg Lys Gln Ile Val Ala Gly Val Asn Tyr Phe
        50                  55                  60

Leu Asp Val Glu Leu Gly Arg Thr Thr Cys Thr Lys Thr Gln Pro Asn
65                  70                  75                  80

Leu Asp Asn Cys Pro Phe His Asp Gln Pro His Leu Lys Arg Lys Ala
                85                  90                  95
```

```
Phe Cys Ser Phe Gln Ile Tyr Ala Val Pro Trp Gln Gly Thr Met Thr
            100                 105                 110

Leu Ser Lys Ser Thr Cys Gln Asp Ala Ser Ala Ser His His His His
        115                 120                 125

His His Gly Ala Glu Thr Ala Gln Ala Lys His Lys Gln Arg Lys Arg
    130                 135                 140

Leu Lys Ser Ser Cys Lys Arg His Pro Leu Tyr Val Asp Phe Ser Asp
145                 150                 155                 160

Val Gly Trp Asn Asp Trp Ile Val Ala Pro Pro Gly Tyr His Ala Phe
                165                 170                 175

Tyr Cys His Gly Glu Cys Pro Phe Pro Leu Ala Asp His Leu Asn Ser
            180                 185                 190

Thr Asn His Ala Ile Val Gln Thr Leu Val Asn Ser Val Asn Ser Lys
        195                 200                 205

Ile Pro Lys Ala Cys Cys Val Pro Thr Glu Leu Ser Ala Ile Ser Met
    210                 215                 220

Leu Tyr Leu Asp Glu Asn Glu Lys Val Val Leu Lys Asn Tyr Gln Asp
225                 230                 235                 240

Met Val Val Glu Gly Cys Gly Cys Arg
                245
```

```
<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: sense Primer human Cystatin C

<400> SEQUENCE: 5
gacgatctag ataacgaggg caaaaatgt ccagtcccgg caagccgcc          49

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: antisense Primer human Cystatin C

<400> SEQUENCE: 6
caggtcaagc ttctagcgac acccacaacc c                           31

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: sense Primer for fusion protein Cystatin C
      BMP-2

<400> SEQUENCE: 7
accacggatc ctccagtccc ggcaagcc                               28

<210> SEQ ID NO 8
<211> LENGTH: 30
<212> TYPE: DNA
<213> ORGANISM: Artificial Sequence
```

```
<220> FEATURE:
<223> OTHER INFORMATION: Description of Artificial Sequence: PCR Primer
<220> FEATURE:
<223> OTHER INFORMATION: antisense Primer for fusion protein Cystatin C
      BMP-2

<400> SEQUENCE: 8
ccgccaagct tctagcgaca cccacaaccc                                       30

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: antisense Primer for fusion protein Cystatin C
      BMP-2

<400> SEQUENCE: 9
cctccaagct tctaatgatg gtgatggtga tggcgacacc cacaaccc                   48

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:
      Spacer molecule
<220> FEATURE:
<223> OTHER INFORMATION: spacer between Cystatin C and BMP-2
<220> FEATURE:
<221> NAME/KEY: CDS
<222> LOCATION: (1)..(42)

<400> SEQUENCE: 10 agc gct agc cat cac cat cac cat cat ggc gcc gag acc gca              42
Ser Ala Ser His His His His His His Gly Ala Glu Thr Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: spacer between Cystatin C and BMP-2

<400> SEQUENCE: 11

Ser Ala Ser His His His His His His Gly Ala Glu Thr Ala
1               5                   10

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      Spacer molecule
<220> FEATURE:
<223> OTHER INFORMATION: spacer between Cystatin C and BMP-2
<220> FEATURE:
<221> NAME/KEY: CDS
<222> LOCATION: (1)..(18)

<400> SEQUENCE: 12 agc ggt ggc ggt ggc ggt                                                18
Ser Gly Gly Gly Gly Gly
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: spacer between Cystatin C and BMP-2

<400> SEQUENCE: 13

Ser Gly Gly Gly Gly Gly
1               5

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Spacer molecule
<220> FEATURE:
<223> OTHER INFORMATION: spacer between Cystatin C and BMP-2
<220> FEATURE:
<221> NAME/KEY: CDS
<222> LOCATION: (1)..(24)

<400> SEQUENCE: 14 agc ggt gtt ggt tct ggt ccg ggt                              24
Ser Gly Val Gly Ser Gly Pro Gly
1               5

<210> SEQ ID NO 15
<211> LENGTH: 8
<212> TYPE: PRT
<213> ORGANISM: Artificial Sequence
<220> FEATURE:
<223> OTHER INFORMATION: spacer between Cystatin C and BMP-2

<400> SEQUENCE: 15

Ser Gly Val Gly Ser Gly Pro Gly
1               5

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      Spacer molecule
<220> FEATURE:
<223> OTHER INFORMATION: spacer between Cystatin C and BMP-2
<220> FEATURE:
<221> NAME/KEY: CDS
<222> LOCATION: (1)..(33)

<400> SEQUENCE: 16 agc gaa caa aaa ctc atc tca gaa gag gat ctg                  33
Ser Glu Gln Lys Leu Ile Ser Glu Glu Asp Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: spacer between Cystatin C and BMP-2

<400> SEQUENCE: 17

Ser Glu Gln Lys Leu Ile Ser Glu Glu Asp Leu
1               5                   10
```

```
<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      Spacer molecule
<220> FEATURE:
<223> OTHER INFORMATION: spacer between Cystatin C and BMP-2
<220> FEATURE:
<221> NAME/KEY: CDS
<222> LOCATION: (1)..(24)

<400> SEQUENCE: 18 agc aac gtt ggt tct ggt ccg ggt                                          24
Ser Asn Val Gly Ser Gly Pro Gly
1               5

<210> SEQ ID NO 19
<211> LENGTH: 8
<212> TYPE: PRT
<213> ORGANISM: Artificial Sequence
<220> FEATURE:
<223> OTHER INFORMATION: spacer between Cystatin C and BMP-2

<400> SEQUENCE: 19

Ser Asn Val Gly Ser Gly Pro Gly
1               5
```

NUCLEIC ACIDS ENCODING CHIMERIC PROTEINS COMPRISING BMP-2 AND A PROTEINASE INHIBITOR

CROSS REFERENCE TO RELATED APPLICATIONS

This application is a 35 U.S.C. §371 National Phase Entry Application from PCT/DE01/01510, filed Apr. 18, 2001 and designating the United States. This application further claims foreign priority to German application DE 100 20 125.3, filed Apr. 18, 2000.

This invention relates to an agent for postoperative use after removal of primary or metastatic bone tumors. This agent applies within the medical field, in particular in the field of orthopedics.

The prognosis for malignant bone tumors has undergone a definite change in the last two decades. In 1970 the five-year survival rate was less than 20%, but today almost 80% of patients survive. This success is attributed to recent therapeutic approaches with pre- or postoperative chemotherapy and/or radiation as well as expansion of the diagnostic and surgical options, which permit a differentiated surgical procedure according to entity, tumor extent and grading. The goal of surgical treatment, apart from a few exceptions, is complete removal of the tumor. There are various options for the procedure in removing a tumor:
(1) preserving the extremity in the original shape, bridging any resulting bone defect (limb salvage),
(2) segment amputation,
(3) amputation, but method (1) is preferred in terms of the patient's quality of life. The following table shows the different resection limits with their pathological results:

Resection limits and pathological evaluation

| | Resection level | Pathological result |
| --- | --- | --- |
| Intracapsular | Intralesional | Resection margin in the tumor |
| Marginal | Extracapsular, but in the accompanying reactive tissue | Reactive tissue, possibly with satellite lesions of the tumor |
| Extensive | In normal tissue, outside of reactive tissue (2 to 3 cm) | Tumor-free, possibly dislocated metastases excised |
| Radical | Extracompartmental | Tumor-free resection margin |

The risks entailed in surgery that salvages the extremity is apparent from the pathological findings, because individual tumor residues may remain if resection is inadequate. These tumor residues can have an extremely negative effect on the patient's prognosis (T. Ozaki, A. Hillmann, N. Lindner, S. Blasius, W. Winkelmann: Chondrosarcoma of the pelvis, Clin. Orthop. 337, 1997, 226–239). In the case of malignant sarcomas of bone and soft tissue, essentially extensive or radical resection is the goal (S. Toma, A. Venturino, G. Sogno, C. Formica, B. Bignotti, S. Bonassi, R. Palumbo: Metastatic bone tumors. Nonsurgical treatment. Outcome and survival, Clin. Orthop. 295, 1993, 246–251). Otherwise, a local recurrence rate of 60–90% must be assumed for marginal resections.

Pre- and/or postoperative treatment of bone tumors by chemotherapy or radiation therapy minimizes the recurrence problem. In addition to the known side effects of this treatment, however, renewed surgical procedures are repeatedly required in a certain percentage of these patients. In addition, not all tumors respond identically to the same treatment strategies. The high incidence of recurrences with a marginal resection in many cases makes an extensive or radical resection appear to be the preferred surgical method. However, the result of such surgery is usually that reconstruction of the bone proves to be complicated. Various options are available for reconstruction of bone:
  autologous reconstruction,
  endoprosthetics and
  allogenic implants.

Autologous reconstruction uses bone material from the patient, which is inserted in place of the bone removed. The possible removal of material is limited here, so that only minor resections can be refilled again. Endoprosthetics consist of replacing the missing bone by prostheses of biocompatible materials. This bone substitute is to some extent very complicated and cost-intensive to manufacture. In treatment of young patients in particular, the problem arises that the prostheses do not adapt to the patient's growth, thus necessitating follow-up surgeries. Allogenic implants presuppose the existence of a functioning bone bank. There is a high incidence of complications in allogenic bone and joint replacement in the traditional sense without a vascular connection. The fracture rate over a period of years is more than 50% in the case of diaphysis implants of the lower extremities, and the infection rate is reported as approximately 10% to 30%.

More recent therapeutic approaches are based on implantation of biodegradable materials coated with recombinant growth factors (C. A. Kirker-Head, T. N. Gerhart, S. H. Schelling, G. E. Hennig, E. Wang, M. E. Holtrop: Long-term healing of bone using recombinant human bone morphogenetic protein 2, Clin. Orthop. 318, 1995, 222–230). Preliminary experiments with recombinant growth factors have already been conducted on animal models (review article: E. H. Groeneveld and E. H. Burger: Bone morphogenetic proteins in human bone regeneration, Eur. J. Endocrinol. 142(1), 2000, 9–21). Methods of producing and using such recombinant growth factors are already known (U.S. Pat. No. 4,472,840, U.S. Pat. No. 4,563,489, U.S. Pat. No. 4,596,574, U.S. Pat. No. 4,789,732, U.S. Pat. No. 4,795,804, U.S. Pat. No. 5,318,898, U.S. Pat. No. 5,393,739, U.S. Pat. No. 5,618,924, European Patent 0,409,472, German Patent 19 748 734). These growth factors serve the purpose of improving the healing of bone defects because they stimulate natural bone growth. However, these factors have no effect on the persistence and possible dissemination of any tumor cells that may still be present postoperatively.

It is also known that the proliferation of osteoblasts may be increased and bone resorption of osteoclasts can be inhibited by a fragment of the HMW (high molecular weight) kininogen known as cysteine proteinase inhibitor (U.S. Pat. No. 5,885,964). The use of this fragment is appropriate when osteogenesis by osteoblasts is diminished due to age and bone resorption by osteoclasts is increased at the same time.

Furthermore, studies of the proteinases involved in tumor metastases and in bone resorption are known (C. Haeckel et al.: Proteinase expression in dedifferentiated parosteal osteosarcoma, Arch. Pathol. Lab. Med. 123, 1999, 213–221; K. Bjornland et al.: S100A4 involvement in metastasis: deregulation of matrix metalloproteinases and tissue inhibitors of matrix metalloproteinases in osteosarcoma cells transfected with an anti-S100A4 ribozyme, Cancer Res. 59, 1999, 4702–4708). The most important enzymes involved in this process are cysteine proteinases (cathepsins L, B), matrix metal proteinases (MMP-2, MMP-9) and the serine proteinase uPA. In addition, it is known that cathepsin K, a cysteine proteinase of osteoclasts, is involved in bone resorption (P. Garnero et al.: The collagenolytic activity of cathepsin K is unique among mammalian proteinases, J. Biol. Chem. 273, 1998, 32347–32352).

Growth factors of the TGF-β superfamily such as the BMPs (bone morphogenetic proteins) are capable of inducing osteoneogenesis. One example is BMP-2, which is described in the following articles: H. Itoh et al.: Experimental spinal fusion with use of recombinant human bone morphogenetic protein 2, Spine 24, 1999, 1402–1405; K. Yoshida et al.: Enhancement by recombinant human bone morphogenetic protein-2 of bone formation by means of porous hydroxyapatite in mandibular bone defects, J. Dent. Res. 78, 1999, 1505–1510. In addition, other BMPs have been described by J. M. Wozney et al.: Novel regulators of bone formation: molecular clones and activities, Science 242, 1988, 1528–1534; S. Oida et al.: Cloning and sequence of bone morphogenetic protein 4 (BMP-4) from a human placental cDNA library, DNA Seq. 5, 1995, 273–275; A. J. Celeste et al.: Identification of transforming growth factor-beta family members present in bone-inductive protein purified from bovine bone, Proc. Natl. Acad. Sci. USA 87, 1990, 9843–9847; E. Ozkaynak et al.: OP-1 cDNA encodes an osteogenic protein in the TGF-beta family, EMBO J. 9, 1990, 2085–2093; E. Ozkaynak et al.: Osteogenic protein-2, A new member of the transforming growth factor-beta superfamily expressed early in embryogenesis, J. Biol. Chem. 267, 1992, 25220–25227; J. Hino et al.: cDNA cloning and genomic structure of human bone morphogenetic protein-3B (BMP-3b), Biochem. Biophys. Res. Commun. 223, 1996, 304–310.

Endogenous proteinase inhibitors are also known. The sequence for human cystatin C was described by M. Abrahamson et al.: Molecular cloning and sequence analysis of cDNA coding for the precursor of the human cysteine proteinase inhibitor cystatin, C. FEBS Lett. 216, 1987, 229–233; the sequence of TIMP-2 was described by W. G. Stetler-Stevenson et al.: Tissue inhibitor of metalloproteinase-2 (TIMP-2) mRNA expression in tumor cell lines and human tumor tissues, J. Biol. Chem. 265, 1990, 13933–13938 and that of PAI-2 was described by R. D. Ye et al.: cDNA cloning and expression in *Escherichia coli* of a plasminogen activator inhibitor from human placenta, J. Biol. Chem. 262, 1987, 3718–3725.

The object of this invention is to create an agent for postoperative use, i.e., after excision of primary or metastatic bone tumors, which supports successful bone regeneration and requires a less stressful surgery for the patient without the risk of a new tumor metastasis to the treated bone. The patient's quality of life should be increased through this type of bone resection with effective and long-lasting control of tumor, whereby it is necessary to take into account not only the surgical procedure for bone resection per se but also the consequences of the procedure.

According to this invention, an agent is prepared from a nucleic acid by linking an essentially known sequence for bone growth promotion and a known proteinase inhibitor by a variable spacer molecule, e.g., an oligonucleotide. This linkage results in a novel active ingredient having two functions.

When this bifunctional agent is used postoperatively after removal of bone tumors, bone growth is supported and also metastasis (through tumor cells remaining in the surgical field) in the marginal zones of the bone prosthesis is inhibited.

Depending on the biological activity of the tumor, micrometastases may be expected in any case, leading to local relapses. In addition to the favorable effect on reconstitution of the bone, the risk of a possible metastasis should be largely minimized. In contrast to practice, it is to be done without a radical resection which has the goal of removing as much bone material that the resection borders are reliably tumor-free in order to effectively combat the tumor. Instead, only a minimum of bone material needs to be resected, whereby the risk of a further metastasis starting from the resection margin is reduced. Because the procedure is minimal, the patient's quality of life is increased not only concerning the surgery and its immediate consequences but also regarding later consequences. Due to the influence of the bifunctional agent, there is also better growth into the prosthesis, which results in shorter recovery times and more stable incorporation of the prosthesis, among other effects. This should also prevent follow-up surgeries.

A DNA according to the invention is described below in the form of a cDNA. This stands exemplarily for any DNA falling under the present invention. The agent is further described as a bifunctional protein and is produced with the help of well-known methods of genetic engineering. The basis of the bifunctional protein may be two independently naturally occurring proteins or domains of proteins, which are linked with one another by means of a spacer molecule (a peptide not belonging to the natural protein domains between the functional domains).

This invention includes the coupling of two cDNAs by an oligonucleotide to form a new cDNA. This invention also includes derivatives of this new cDNA, which are formed by replacement, insertion, or deletion of one or more nucleotides, where the activity of the coded gene product is preserved. An object of this invention is also recombinant expression of the bifunctional protein in prokaryotes such as *E. coli* strains. This is done by using vectors, which permit expression in prokaryotic cells. These vectors contain suitable well-known regulation signals for gene expression such as promoters and ribosome binding sites. The promotors used include, for example, the T7 promotor, the tac promotor and the tet promotor. The vectors also code for antibiotic resistence and the replication origin.

The cDNA of the bifunctional protein is used for in vitro and in vivo transfection of suitable cell cultures such as cells of mesenchymal origin. Transfection is understood to refer to the insertion of nucleic acid constructs into cells or tissue. To do so, vectors containing well-known and suitable regulation signals for gene expression are used. These include transcription signals such as promoters, enhancers, and polyadenylation sites as well as translation signals such as ribosome binding sites. Promotors used include eukaryotic promoters of viral and cellular origin such as the CMV promotor, the RSV promotor or the -actin promotor. All known polyadenylation signals may be used as the polyadenylation signal, e.g., that of SV40. These vectors may additionally contain genetic markers such as antibiotic resistance genes. Furthermore, viral vectors are also suitable for transfection of cells.

DNA constructs for prokaryotic and eukaryotic expression are produced by the well-known methods of genetic engineering such as PCR and cloning.

Figure 4:
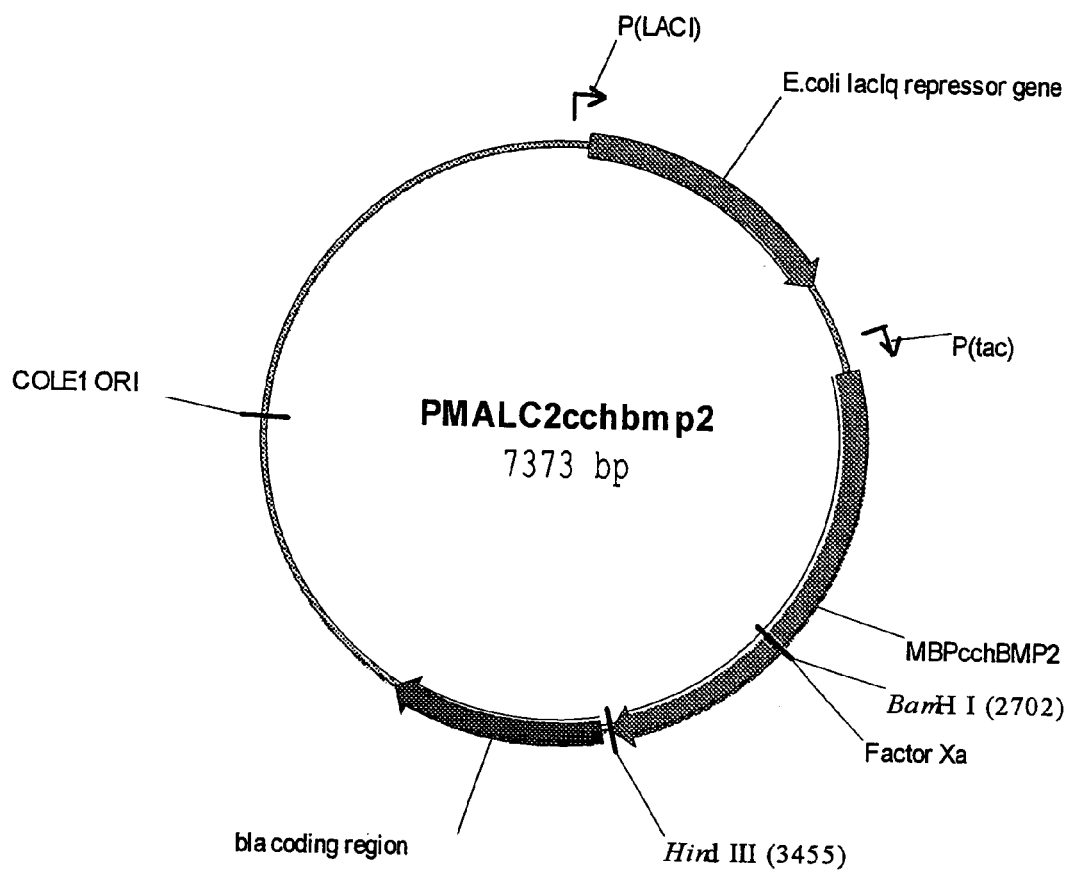

This invention will now be explained in greater detail on the basis of exemplary embodiments illustrated in the drawings, which show:

| | |
|---|---|
| FIG. 1 | primer used in PCR |
| FIG. 2 | expression plasmid for the fusion protein of cystatin C and BMP-2 |
| FIG. 3 | examples of possible oligonucleotides for linking the fusion partners |
| FIG. 4 | expression plasmid for the fusion protein of cystatin C and BMP-2 in a plasmid with maltose binding protein (MBP) |

Embodiment 1:

Producing the Prokaryotic Expression Plasmid

The cDNA of human cystatin C was amplified by means of primers A and B shown in FIG. 1 for the polymerase chain reaction (PCR) from a plasmid (M. Abrahamson et al.: Molecular cloning and sequence analysis of cDNA coding for the precursor of the human cysteine proteinase inhibitor cystatin C, FEBS Lett. 216, 1987, 229–233). The cDNA of a mature human BMP-2 was obtained from the plasmid pBF008 (B. Fahnert, HKI Jena) by restriction digestion with the restriction endonucleases Eco47III and HindIII. Both cDNAs were cloned consecutively in reading frame in the expression plasmid pASK75 (Biometra). For this purpose firstly the PCR product of human cystatin C was cloned in the vector pCR2.1-TOPO (Invitrogen) and then the correctness of the PCR product was checked with the LICOR system. The cDNA of human cystatin C was cut out by restriction digestion with the enzymes XbaI and Eco47III and was ligated into the vector pASK75, which was cleaved with the same restriction enzymes. The resulting construct (pASKcC) was digested with the restriction enzymes Eco47III and HindIII. The cDNA of the mature human BMP-2 cut out of the plasmid pBF008 with the same restriction enzyme was ligated into the previously cleaved plasmid pASK75cC. A peptide consisting of six histidines (SEQ ID NO. 10), located on the N-terminus of the cDNA of mature human BMP-2, was used as a possible spacer between the two cDNAs in the cloning strategy described here (see also SEQ ID NOS. 12, 14, 16, 18). The base sequence in the regions of the DNA construct that were of interest was checked by DNA sequencing using the LICOR system, and it was verified that the reading frame is correct. FIG. 2 shows the resulting expression plasmid (pASKcCHBMP-2). FIG. 3 shows examples of possible oligonucleotides for linking the fusion partners. Exemplarily cystatin C is mentioned as an inhibitor and BMP-2 as a growth factor. For example, PAI-2 could also be used as a proteinase inhibitor for serine proteinases, or TIMP-2 could be used as an inhibitor for metalloproteinases. Other growth factors that could be used include BMP-3, BMP-4, BMP-7 and other representatives of the TGF-β superfamily.

The cDNA of the bifunctional protein (cCHBMP-2) was amplified by PCR with primers C, D and optionally D' (FIG. 1) and inserted in the plasmid pMALc2 (New England BioLabs). For this purpose the PCR product cCHBMP-2 was cloned in the vector pCR2.1-TOPO and was cut out with the restriction enzymes BamHI and HindIII. The plasmid pMALc2 was digested with the same restriction enzymes. The two cDNAs were ligated together. The resulting expression plasmid was sequenced in the region of interest. This expression plasmid (pMALc2cCHBMP-2, FIG. 4) was used for expression of the bifunctional protein as a fusion protein with another protein, the protein MBP (maltose binding protein). MBP is used for purification of recombinant proteins by affinity chromatography. It can be removed again by factor Xa cleavage after purification, so that the authentic N-terminus of cystatin C is preserved.

Embodiment 2:

Expression of the Bifunctional Protein in E. coli (BL21 (DE3))

For the purpose of expression, the expression plasmids pASKcCHBMP-2 (FIG. 2) and pMALc2cCHBMP-2 (FIG. 4), which are described in Embodiment 1, were transformed in the bacterial strain BL21 (DE3) (Novagen). The transformation was performed by well-known methods for chemically competent cells.

Expression was performed as follows. 200 mL Terrific broth (TB) medium with 100 g/mL ampicillin was inoculated with a single clone and cultured. Expression was induced by adding 100 g/L anhydrotetracycline in the case of plasmid paskcCHBMP-2 and by adding 1 mM IPTG in the case of plasmid pMalc2cCHBMP-2.

The bacteria were harvested by centrifugation and disrupted by well-known methods with lysis buffer and sonication. This material was purified by chromatography on Ni-NTA resin under denaturing conditions.

The folding and dimerization were performed in a dimerization buffer at 25° C. over a period of several days.

In addition to expression in bacteria, which is presented here as an example, expression in other known expression systems such as yeasts, insect cells or mammalian cells is also possible.

The invention claimed is:

1. An isolated nucleic acid encoding a bifunctional protein comprising:
   (a) an isolated nucleic acid encoding bone growth factor BMP-2 capable of inducing osteogenesis;
   (b) an isolated nucleic acid encoding a proteinase inhibitor,
   wherein said nucleic acid of (a) is linked to said nucleic acid of (b) via an oligonucleotide, and wherein said so linked nucleic acids encode a bifunctional protein.

2. The nucleic acid encoding a bifunctional protein of claim 1, wherein said nucleic acid encoding the proteinase inhibitor is a sequence encoding a cysteine proteinase inhibitor or a functional fragment thereof and wherein said functional fragment retains the function of said proteinase inhibitor encoded by said nucleic acid of (b).

3. The nucleic acid encoding a bifunctional protein of claim 1, wherein said nucleic acid encoding the proteinase inhibitor is a sequence encoding a serine proteinase inhibitor or a functional fragment thereof and wherein said functional fragment retains the function of said proteinase inhibitor encoded by said nucleic acid of (b).

4. The nucleic acid encoding a bifunctional protein of claim 1, wherein said nucleic acid encoding the proteinase inhibitor is a sequence encoding a metalloproteinase inhibitor or a functional fragment thereof and wherein said functional fragment retains the function of said proteinase inhibitor encoded by said nucleic acid of (b).

5. The nucleic acid encoding a bifunctional protein of claim 1, wherein the oligonucleotide linking (a) and (b) is SEQ ID NO: 10 or a functional fragment thereof.

6. The nucleic acid encoding a bifunctional protein of claim 1, wherein the oligonucleotide linking (a) and (b) is chosen from the group consisting of SEQ ID NO: 12, 14, 16, 18, or a functional fragment thereof.

7. A method for producing a bifunctional protein, said method comprising:
   (a) providing an isolated nucleic acid encoding BMP-2 capable of inducing osteogenesis,
   (b) linking said isolated nucleic acid to another isolated nucleic acid encoding a proteinase inhibitor via an oligonucleotide, and
   expressing said bifunctional protein in vitro,
   wherein said bifunctional protein retains the functions of said bone growth factor BMP-2 and said proteinase inhibitor.

8. The method of claim 7, wherein said nucleic acid encoding the proteinase inhibitor is a sequence encoding a cysteine proteinase inhibitor or a functional fragment thereof and wherein said functional fragment retains the function of said proteinase inhibitor encoded by said nucleic acid of (b).

9. The method of claim 7, wherein said nucleic acid encoding the proteinase inhibitor is a sequence encoding a serine proteinase inhibitor or a functional fragment thereof and wherein said functional fragment retains the function of said proteinase inhibitor encoded by said nucleic acid of (b).

10. The method of claim 7, wherein said nucleic acid encoding the proteinase inhibitor is a sequence encoding a metalloproteinase inhibitor or a functional fragment thereof and wherein said functional fragment retains the function of said proteinase inhibitor encoded by said nucleic acid of (b).

11. The method of claim 7, wherein the oligonucleotide linking the BMP-2 and proteinase inhibitor encoding sequences is SEQ ID NO: 10 or a functional fragment thereof.

12. The method of claim 7, wherein the oligonucleotide linking the BMP-2 and proteinase inhibitor encoding sequences is chosen from the group consisting of SEQ ID NO: 12, 14, 16, 18, or a functional fragment thereof.

13. A method for producing a nucleic acid encoding a bifunctional protein, said method comprising (a) providing an isolated nucleic acid encoding a BMP-2 capable of inducing osteogenesis,
(b) linking said isolated nucleic acid to another isolated nucleic acid encoding a proteinase inhibitor via an oligonucleotide, wherein the so linked nucleic acids encode said bifunctional protein,
wherein said bifunctional protein retains the two functions of said BMP-2 and said proteinase inhibitor encoded by said nucleic acids of (a) and (b).

14. The method of claim 13, wherein the nucleic acid encoding the proteinase inhibitor is a sequence encoding a cysteine proteinase inhibitor or a functional fragment thereof.

15. The method of claim 13, wherein the nucleic acid encoding the proteinase inhibitor is a sequence encoding a serine proteinase inhibitor or a functional fragment thereof.

16. The method of claim 13, wherein the nucleic acid encoding the proteinase inhibitor is a sequence encoding a metalloproteinase inhibitor or a functional fragment thereof.

17. The method of claim 13, wherein the oligonucleotide is encoded by SEQ ID NO: 10 or a functional fragment thereof.

18. The method of claim 13, wherein the oligonucleotide is chosen from the group consisting of SEQ ID NO: 12, 14, 16, 18, or a functional fragment thereof.

* * * * *